United States Patent [19]

Felder et al.

[11] 4,271,294
[45] Jun. 2, 1981

[54] AMINOALKOXY DERIVATIVES OF AROMATIC KETONES

[75] Inventors: Louis Felder, Basel; Rudolf Kirchmayr, Aesch; Rinaldo Küsler, Binningen, all of Switzerland

[73] Assignee: Ciba-Geigy Corporation, Ardsley, N.Y.

[21] Appl. No.: 129,876

[22] Filed: Mar. 13, 1980

Related U.S. Application Data

[63] Continuation of Ser. No. 968,889, Dec. 13, 1978, abandoned.

[30] Foreign Application Priority Data

Dec. 22, 1977 [CH] Switzerland .................. 15883/77

[51] Int. Cl.³ .................. C07C 97/10; C07D 265/30; C07D 241/04; C07D 211/08
[52] U.S. Cl. .................. 544/87; 260/326.56; 260/326.5 J; 544/174; 544/175; 544/357; 544/399; 546/190; 546/237; 564/342; 564/344; 564/345
[58] Field of Search .................. 544/87, 357; 546/190; 260/326.5 G; 564/342, 344, 345

[56] References Cited

U.S. PATENT DOCUMENTS 3,715,293  2/1973  Sandner et al. .................. 204/159.14

FOREIGN PATENT DOCUMENTS 2337813  2/1974  Fed. Rep. of Germany .

*Primary Examiner*—Richard Raymond
*Attorney, Agent, or Firm*—Luther A. R. Hall

[57] ABSTRACT

Compounds of the formula I

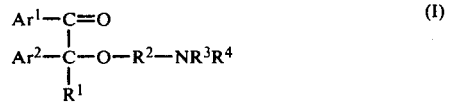

wherein $Ar^1$ and $Ar^2$ represent unsubstituted or substituted phenyl, $R^1$ represents hydrogen, alkyl, alkoxy, hydroxyalkyl, allyl, benzyl or a group $—O—R^2-NR^3R^4$, $R^2$ represents alkylene and $—NR^3R^4$ is an open chain or cyclic organic amino group, are effective initiators for the photopolymerization of unsaturated compounds or for the photocrosslinking of polyolefins. They can be obtained by different methods which are in themselves known, in particular by reaction of the corresponding haloalkyl ethers or haloalkyl ketals with primary or secondary amines.

6 Claims, No Drawings

AMINOALKOXY DERIVATIVES OF AROMATIC KETONES

This is a continuation of application Ser. No. 968,889, filed on Dec. 13, 1978 now abandoned.

The invention relates to novel initiators for the photopolymerisation of unsaturated compounds or for the photochemical crosslinking of polyolefins, and to the systems containing such initiators.

The photoinitiators of the present invention are compounds of the formula (I)

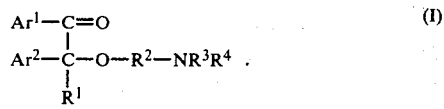

wherein $Ar^1$ and $Ar^2$, each independently of the other, represent phenyl or phenyl which is substituted by $C_1$–$C_4$-alkyl, $C_1$–$C_4$-alkoxy or halogen, $R^1$ represents hydrogen, $C_1$–$C_4$-alkyl, benzyl, allyl, $C_1$–$C_4$-alkoxy, hydroxymethyl or a group $-O-R^2-N(R^3)(R^4)$, $R^2$ represents $C_2$–$C_4$-alkylene, $R^3$ represents hydrogen, $C_1$–$C_{12}$-alkyl, allyl, benzyl, cyclohexyl, $C_2$–$C_4$-hydroxyalkyl or $C_3$–$C_8$-alkoxyalkyl, and $R^4$ represents $C_1$–$C_{12}$-alkyl, allyl, $C_2$–$C_4$-hydroxyalkyl, $C_3$–$C_8$-alkoxyalkyl, cyclohexyl, benzyl or phenyl, or $R^3$ and $R^4$ together represent alkylene or oxaalkylene of 4 to 5 carbon atoms or a group $-CH_2CH_2-NR^5-CH_2CH_2-$ and $R^5$ represents hydrogen or $C_1$–$C_4$-alkyl.

In particular, the photoinitiators are compounds of the formula (I), wherein $Ar^1$ and $Ar^2$, each independently of the other, represent phenyl or phenyl which is substituted by $C_1$–$C_4$-alkyl, $C_1$–$C_4$-alkoxy or halogen, $R^1$ represents hydrogen, $C_1$–$C_4$-alkyl, benzyl, hydroxymethyl, or a group $-O-R^2-NR^3R^4$, $R^2$ represents $C_2$–$C_4$-alkylene, $R^3$ represents hydrogen, $C_1$–$C_{12}$-alkyl, allyl, $C_2$–$C_4$-hydroxyalkyl or $C_3$–$C_8$-alkoxyalkyl, and $R^4$ represents $C_1$–$C_{12}$-alkyl, allyl, $C_2$–$C_4$-hydroxyalkyl, $C_3$–$C_8$-alkoxyalkyl, cyclohexyl, benzyl or phenyl, or $R^3$ and $R^4$ together represent $C_4$–$C_5$-alkylene or oxaalkylene.

$Ar^1$ and $Ar^2$ can be for example chlorophenyl, bromophenyl, tolyl, xylyl or methoxyphenyl, but are preferably phenyl.

$R^1$ as alkyl can be methyl, ethyl, propyl or butyl, and $R^1$ as alkoxy can be methoxy, ethoxy, propoxy or butoxy.

$R^2$ can be for example 1,2-ethylene, 1,3-propylene, 1,2-propylene or 1,2-butylene.

The group $-NR^3R^4$ can be for example dimethylamino, diethylamino, dibutylamino, di-2-ethylhexylamino, didecylamino, di-dodecylamino, di-2-hydroxyethylamino, di-2-hydroxypropylamino, methyl-2-hydroxyethylamino, di-2-methoxyethylamino, di-2-butoxyethylamino, dicyclohexylamino, ethylcyclohexylamino, butylbenzylamino, benzylamino, cyclohexylamino, methylphenylamino, 2-hydroxyethylphenylamino, pyrrolidino, piperidino, morpholino, piperazino or 4-methylpiperazino.

If $R^1$ is hydrogen or alkyl, the compounds of the formula I are aminoalkylbenzoin ethers. If $R^1$ is alkoxy or a group $-O-R^2-NR^3R^4$, the compounds of the formula I are benzil monoketals which contain amino groups in the alcohol residue. Benzoin ethers and benzil monoketals which carry no amino groups are known compounds. Their use as photosensitizers has been described for example in British Pat. Nos. 1,156,460 and 1,254,231, in U.S. Pat. No. 3,715,293 and in German Offenlegungsschriften 2,232,365 and 2,337,813.

The compounds of the formula I are novel compounds which can also be used as sensitizers in the photopolymerisation of unsaturated compounds as well as in the photochemical cross-linking of polyolefins. Compared with the known compounds which do not contain amino groups, they are distinguished by an increased effectiveness as photosensitizers, which is observed in the fact that shorter exposure times are necessary for curing unsaturated compounds and for crosslinking polyolefins. This feature corresponds to a greater output per unit of time and per exposure installation when the novel compounds are used in industrial production plants.

Preferred compounds are those of the formula I, wherein $Ar^1$ and $Ar^2$ represent phenyl, $R^1$ represents hydrogen, $C_1$–$C_4$-alkyl or a group $-O-R^2$-$NR^3R^4$, $R^2$ represents 1,2-ethylene, each of $R^3$ and $R^4$ represents $C_1$–$C_4$-alkyl or $R^3$ and $R^4$ together represent $-(CH_2)_5-$, $-CH_2CH_2OCH_2CH_2-$ or $-CH_2CH_2-NR^5-CH_2CH_2-$ and $R^5$ represents hydrogen or $CH_3$.

The compounds of the formula I, wherein $R^1$ is hydrogen or alkyl, can be prepared in general by reaction of the corresponding halogenalkyl benzoin ether with an amine of the formula $R^3-NH-R^4$ in the presence of bases:

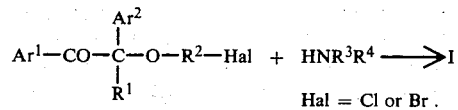

An excess of the amine can also be used as base.

Another general method of manufacture is the reaction of the corresponding α-halogen ketones with the alkali compounds of amino alcohols:

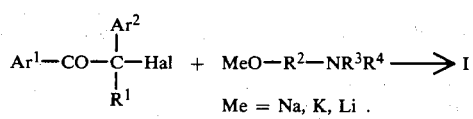

The compounds of the formula I, wherein $R^1$ is a group $-O-R^2-NR^3R^4$, can be prepared in general from the corresponding halogenalkyl ketals by reaction with amines of the formula $R^3-NH-R^4$:

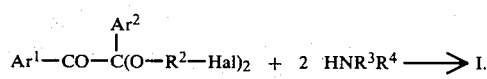

Another method of manufacture consists in the partial or complete transacetylsation of the readily obtainable lower alkyl ketals with amino alcohols:

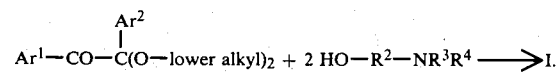

Examples of compounds of the formula I, wherein $R^1$ is hydrogen or alkyl, are:
benzoin-2-dimethylaminoethyl ether
benzoin-2-dibutylaminoethyl ether
benzoin-2-morpholinoethylether benzoin-2-piperidinoethylether
benzoin-2-piperazinoethylether
benzoin-2-pyrrolidinopropylether
α-methyl-benzoin-2-morpholinoethylether
α-benzyl-benzoin-2-piperidinoethylether
α-allyl-benzoin-2-piperidinoethylether
α-hydroxymethyl-benzoin-2-morpholinoethylether
benzoin-2-dihydroxyethylaminoethylether
benzoin-2-dimethoxyethylaminoethylether
4,4'-dichlorobenzoin-(2-morpholinoethyl)ether.

Examples of compounds of the formula I, wherein $R^1$ represents an alkoxy or aminoalkoxy group, are:
benzil-di-(2-ethylaminoethyl)ketal
benzil-di-(2-dimethylaminoethyl)ketal
benzil-di-(2-morpholinoethyl)ketal
benzil-methyl-2-morpholinoethylketal
benzil-di-(2-piperidinoethyl)ketal
benzil-methyl-2-piperidinoethylketal
benzil-di-(2-piperidinoethyl)ketal
4,4'-dichlorobenzil-di-(2-diethylaminopropyl)ketal
4,4'-dichlorobenzil-di-[2-(ethyl-phenylamino)ethyl]-ketal
benzil-di-[2-(4-methylpiperazino)-ethylketal
2,2'-dimethoxybenzil-di-(3-piperidinopropyl)ketal
4,4'-dimethylbenzil-di-(2-pyrrolidinoethyl)ketal.

The compounds of the formula I can be used as sensitizers for the photopolymerisation of unsaturated compounds or systems which contain such compounds.

Such photopolymerisable compounds are for example unsaturated monomers, such as esters of acrylic or methacrylic acid, for example methylacrylate, ethylacrylate, n-or tert-butylacrylate, isooctylacrylate or hydroxyethylacrylate, methyl- or ethylmethacrylate, ethylene diacrylate, neopentyl diacrylate, trimethylolpropane trisacrylate, pentaerythritol tetraacrylate or pentaerythritol trisacrylate; acrylonitrile, methacrylonitrile, acrylamide, methacrylamide, N-substituted acrylamides and methacrylamides; vinyl esters, such as vinyl acetate, vinyl propionate, vinyl acrylate or vinyl succinate; other vinyl compounds, such as vinyl ethers, styrene, alkyl styrenes, halostyrenes, divinyl benzene, vinyl naphthalene, N-vinylpyrrolidone, vinyl chloride or vinylidene chloride; allyl compounds, such as diallyl phthalate, diallyl maleate, triallyl isocyanurate, triallyl phosphate or ethylene glycol diallyl ether and the mixtures of such unsaturated monomers.

Photopolymerisable compounds are in addition unsaturated oligomers or polymers and their mixtures with unsaturated monomers. These include thermoplastic resins which contain unsaturated groups, such as fumaric acid ester ester grous, allyl groups or acrylate or methacrylate groups. These unsaturated groups are usually bonded through functional groups to the main chain of these linear polymers. Mixtures of oligomers with simply and poly-unsaturated monomers are very important. Examples of such oligomers are unsaturated polyesters, unsaturated acrylic resins and isocyanate or epoxide modified acrylate oligomers as well as polyether acrylate oligomers. Examples of poly-unsaturated compounds are in particular the acrylates of diols and polyols, for example hexamethylene diacrylate or pentaerythritol tetracrylate. Acrylates are also preferred as simply unsaturated monomers, for example butyl acrylate, phenyl acrylates, benzyl acrylate, 2-ethylhexyl acrylate or 2-hydroxypropyl acrylate. By choosing from the different representatives of the three components, the opportunity is afforded to vary the consistency of the unpolymerised mixture as well as the plasticity of the polymerised resin.

In addition to these three-component mixtures, two-component mixtures especially are of great importance among the polyester resins. These usually consist of an unsaturated polyester and a vinyl compound. The unsaturated polyesters are oligomer esterification products of at least one unsaturated dicarboxylic acid, for example maleic, fumaric or citraconic acid, and usually of at least one saturated dicarboxylic acid, for example phthalic acid, succinic acid, sebacic acid or isophthalic acid, with glycols, for example ethylene glycol, propanediol-1,2, di- or triethylene glycol or tetramethylene glycol, whilst monocarboxylic acids and monoalcohols are generally also concurrently employed for the modification. These unsaturated polyesters are normally dissolved in a vinyl or allyl compound, styrene being preferably used for this purpose.

Photopolymerisable systems which are used for the different purposes usually contain, in addition to the photopolymerizable compounds and the photosensitizer, a number of other ingredients. It is therefore often customary to add heat inhibitors in order to prevent a premature polymerisation, especially during the preparation of the systems by mixing the components. Hydroquinone, hydroquinone derivatives, p-methoxyphenyl, β-naphthylamine or β-naphthols are used for example for this purpose. Furthermore, small amounts of UV absorbers can be added, for example those of the benztriazole or benzophenone type.

To increase the storage life in the dark, it is possible to add copper compounds, such as copper naphthenate, copper stearate or copper octaoate, phosphorus compounds, such as triphenylphosphine, tributylphosphine, triethyl phosphite, triphenyl phosphite or tribenzyl phosphate, quaternary ammonium compounds, such as tetramethylammonium chloride or trimethylbenzylammonium chloride, or hydroxylamine derivatives, for example N-diethylhydroxylamine. In addition, the photopolymerisable systems can contain chain transfer agents, for example N-methyl-diethanolamine, triethanolamine or cyclohexene.

In order to exclude the inhibiting action of atmospheric oxygen, paraffin or similar wax-like substances are frequently added to photohardening systems. On account of their poor solubility in the polymer, these substances float at the beginning of the polymerisation and form a transparent surface layer which prevents the entry of air. The atmospheric oxygen can also be deactivated by introducing autoxidisable groups, for example allyl groups, into the resin to be hardened.

Depending on the end-use, photopolymerisable systems also contain fillers, such as silicic acid, talc or gypsum, pigments, dyes, fibres, thixotropic agents or levelling agents.

The photosensitizers of the invention can also be used in combination with radical initiators, for example peroxides, hydroperoxides, ketone peroxides or percarboxylic acid esters.

Combinations with known photosensitizers, such as benzoin ethers, dialkoxy acetophenones or benzyl ketals, or combinations with aromatic ketones, can also be used. Examples of such ketones are benzophenone, substituted benzophenone derivatives, Michler's ketone, anthraquinone and anthraquinone derivatives, as well as thioxanthone and the derivatives thereof.

Photohardening is of great importance for printing inks, since the drying time of the binder is a decisive factor in the production speed of printing products and should be in the order of fractions of seconds. The sensitizers of the invention are also very suitable for photohardening systems for the manufacture of printing plastes. Mixtures of soluble linear polyamides with photopolymerisable monomers, for example acrylamides, and a photosensitizer, are usually employed for this purpose. Films or plates prepared from these systems are exposed via the negative (or positive) of the original and the unhardened portions are subsequently eluted with a solvent.

A further field of use of UV hardening is metal coating, for example in the varnish coating of metal sheeting for tubes, cans or bottle caps, as well as the UV hardening of plastic coatings, for example of floor or wall coverings based on PVC.

Exemplary of the UV hardening of paper coatings is the colourless varnish coating of labels, gramophone record sleeves or book jackets.

According to the invention, the compounds of the formula I can also be used as sensitizers for the photochemical crosslinking of polyolefins, for example polypropylene, polybutene, polyisobutylene and also copolymers, for example ethylene/propylene copolymers, but preferably polyethylene of low, medium or high density.

The photosensitizers are advantageously used for the above fields of use in amounts of 0.1 to 20% by weight, preferably about 0.5 to 5% by weight, based on the photopolymerisable of crosslinkable system. The term "system" is to be understood as meaning the mixture of the photopolymerisable or crosslinkable compound, the photosensitizer and the other fillers and additives, as it is used in the respective application.

The addition of the photosensitizers to the photopolymerisable systems is accomplished in general by simple stirring, since most of these systems are fluid or readily soluble. Usually the sensitizers of the invention dissolve in the system, thereby ensuring their uniform distribution and the transparency of the polymers.

The polymerisation is carried out by the known methods of polymerisation by irradiation with light which is rich in shortwave radiation. Suitable light sources are for example mercury medium pressure, high pressure and low pressure lamps, as well as superactinic fluorescent tubes, the emission peaks of which are in range between 250 and 400 nm.

In the photochemical crosslinking of polyolefins, the photosensitizer is added to the polyolefin before or during the moulding, for example by mixing in powder form or by mixing with the plasticised polyolefin. The crosslinking is effected by irradiation of the moulded article in solid form, for example in the form of sheets or fibres.

The following Examples describe the manufacture and use of compounds of the formula I in more detail. Parts and percentages are by weight.

EXAMPLE 1

Benzil-di-(2-morpholinoethyl)ketal (2,2-di-(2-morpholino-ethoxy)-1,2-diphenyl-ethanone)

With stirring, 35 g (0.1 mole) of benzil-di-(2-chloroethyl)ketal and 52 g (0.6 mole) of morpholine are kept for 6 hours at 110° C. After cooling, the product is taken up in ether. The ether layer is washed with water, dried over $Na_2SO_4$ and concentrated. The residual oil is dried in a high vacuum at 50°–60° C.

Yield: 41 g (91%). $C_{26}H_{34}N_2O_5$ calculated: C: 68.70; H: 7.54; N: 6.16%; found: C: 68.7; H: 7.7; N: 6.1%.

EXAMPLE 2

A resin mixture consisting of 80 parts of Plex 6616 (acrylate resin marketed by Röhm, Darmstadt), 20 parts of trimethylolpropane trisacrylate and 2 parts of the photoinitiator of Example 1 is drawn out to a thickness of 40μ on glass plates using a film drawing device. The films are exposed to air for about 20 seconds and subsequently irradiated with a mercury medium pressure lamp (Hanovia device, Model 45080). The samples are passed under the UV lamp on a moving belt at such a speed as to give an effective irradiation time of 0.16 seconds per passage. Under these conditions, 7 passages are necessary to obtain a non-tacky film. The hardness of the film in the oscillation test using the pendulum apparatus according to König is 124 after 7 passages, 127 after 9 passages and 139 after 11 passages.

EXAMPLE 3

Benzil-di-(2-diethylaminoethyl)ketal (2,2-di-(2-diethylaminoethoxy)-1,2-diphenyl-ethanone)

20 g (0.057 mole) of benzil-di-(2-chloroethyl)ketal are stirred with 150 g (2.05 moles) of diethylamine for 24 hours at 140° C. in a pressure autoclave. After cooling, the reaction mixture is taken up in ether and extracted with water. The ether layer is dried over $Na_2SO_4$ and concentrated. The residual oil is dried in a high vacuum.

| $C_{26}H_{38}N_2O_3$ | calculated : | found : |
|---|---|---|
| | C 73.20% | C 73.20% |
| | H 8.95% | H 9.1% |
| | N 6.57% | N 6.3% |

EXAMPLE 4

Benzoin-2-morpholinoethyl ether (2-(2-morpholinoethoxy)-1,2-diphenyl-ethanone)

55 g (0.2 mole) of benzoin-2-chloroethyl ether are stirred with 174 g of morpholine for 6 hours at room temperature and for 1 hour at 130° C. After cooling, the reaction mixture is diluted with ether and poured into water. The aqueous layer is extracted with ether and the ether layer is washed neutral with $H_2O$. The ether layer is then extracted with dilute hydrochloric acid. The hydrochloric acid solution is made alkaline with $K_2CO_3$ and extracted with ether. The ether layer is dried over $Na_2SO_4$ and concentrated. The residual oil is dried in vacuo.

| $C_{19}H_{23}NO_3$ | calculated : | found : |
|---|---|---|
| | C 73.82% | C 73.5% |
| | H 7.13% | H 7.3% |
| | N 4.31% | N 4.5% |

EXAMPLE 5

Benzoin-2-diethylaminoethyl ether (2-(2-diethylaminoethoxy)-1,2-diphenyl-ethanone)

14 g (0.05 mole) of benzoin-2-chloroethyl ether are stirred with 75 g of diethylamine for 24 hours at 55° C. After cooling, the reaction mixture is diluted with ether and extracted with dilute hydrochloric acid. The aqueous layer is made alkaline with $K_2CO_3$ and extracted with ether. The ether layer is washed with ice water, dried over $Na_2SO_4$ and concentrated. The residual oil is dried in a high vacuum.

| $C_{20}H_{25}NO_2$ | calculated: | found: |
|---|---|---|
| | C 77.14% | C 76.9% |
| | H 8.09% | H 8.1% |
| | N 4.50% | N 4.4% |

EXAMPLE 6

Benzoin-2-piperazinoethyl ether (2-(2-piperazinoethoxy)-1,2-diphenyl-ethanone)

27 g (0.1 mole) of benzoin 2-chloroethyl ether and 34 g (0.4 mole) of piperazine are heated to 70° C. After 1½ hours, 5 ml of toluene are added in order to prevent the piperazine from subliming and the mixture is heated to 140° C. and kept for 2 hours at reflux temperature. After cooling, the reaction mixture is diluted with ether and extracted with dilute hydrochlorid acid. The hydrochloric acid solution is freed from ether and neutralised with $K_2CO_3$. The alkaline solution is extracted with ether and then with toluene. The toluene solution is dried over $Na_2SO_4$ and concentrated. The residual oil is dried in a high vacuum at 60° C.

| $C_{20}H_{24}N_2O_2$ | calculated : | found : |
|---|---|---|
| | C 74.05% | C 74.2% |
| | H 7.46% | H 7.7% |
| | N 8.64% | N 9.0% |

EXAMPLE 7

Benzoin-2-piperidinoethyl ether (2-(2-piperidinoethoxy)-1,2-diphenyl-ethanone)

With stirring, 27 g (0.1 mole) of benzoin-2-chloroethyl ether and 68 g (0.8 mole) of piperidine are kept for 6 hours at 110° C. After cooling, the product is taken up in ether and the ether layer is washed with water, dried over $Na_2SO_4$ and concentrated. The residual oil is taken up in hexane and the crystals obtained are recrystallised from hexane. Melting point: 53° C.

| $C_{21}H_{25}NO_2$ | calculated : | found : |
|---|---|---|
| | C 77.99% | C 77.7% |
| | H 7.80% | H 7.8% |
| | N 4.33% | N 4.8% |

EXAMPLE 8

Benzil-di-(2-piperidinoethyl)ketal (2,2-di-(2-piperidinoethoxy)-1,2-diphenyl-ethanone)

With stirring, 35 g (0.1 mole) of benzil-di-(2-chloroethyl)ketal and 77 g (0.9 mole) of piperidine are kept for 7 hours at 105° C. After cooling, the reaction mixture is diluted with ether and the piperidine hydrochloride is collected by filtration. The ether is distilled off and the residual oil is dried in a high vacuum.

| $C_{28}H_{38}N_2O_3$ | calculated : | found : |
|---|---|---|
| | C 74.63% | C 74.6% |
| | H 8.50% | H 9.0% |
| | N 6.22% | N 6.6% |

EXAMPLE 9

Benzil-di-(2-(4-methylpiperazino ethyl) ketal (2,2-di-(2-(4-methylpiperazino)ethoxy)-1,2-diphenyl-ethanone)

With stirring, 23.6 g (0.067 mole) of benzil-di-(2-chloroethyl)ketal and 120 g (1.2 moles) of N-methylpiperazine are kept for 3 hours at 95° C. After cooling, 250 ml of toluene are added and the reaction mixture is poured into water. The aqueous layer is extracted with toluene and the toluene layer is subsequently washed neutral with water. The toluene layer is dried over $Na_2SO_4$, concentrated and dried in a high vacuum.

| $C_{28}H_{40}N_3O_3$ | calculated : | found : |
|---|---|---|
| | C 69.97% | C 70.0% |
| | H 8.39% | H 8.5% |
| | N 11.66% | N 11.1% |

EXAMPLE 10

A resin mixture consisting of 70 parts of Ebecryl 593 (polyester acrylate marketed by UCB, Belgium), 30 parts of trimethylolpropanetriacrylate, 0.5 part of Byk 300 (levelling agent, marketed by Byk-Mallinckrodt, Germany) and 3 parts of photoinitiator, is spread on glass plates in layers having a thickness of 30 to 40μ using a drawing rod. After being exposed to air briefly, these films are cured in a UV laboratory device (Model PPG, QC processor) by irradiation with a UV lamp of 80 watt/cm. After the UV curing, the films are stored under normal climatic conditions and the hardness using the pendulum apparatus according to König is determined. The hardness values as a function of the rate of transportation in the irradiation device are reported in the following table:

| Photoinitiator | Pendulum hardness in secs at transportation speeds of | | |
|---|---|---|---|
| | 10 m/min | 25 m/min | 75 m/min |
| benzil dimethyl ketal (comparison substance) | 151 | 143 | 92 |
| compound of Example 3 | 158 | 155 | 114 |
| compound of Example 4 | 147 | 136 | 76 |
| compound of Example 5 | 129 | 103 | 45 |
| compound of Example 6 | 136 | 121 | 63 |
| compound of Example 7 | 134 | 104 | 64.5 |
| compound of Example 8 | 152 | 145 | 120 |

EXAMPLE 11

α-Methylbenzoin 2-(4-methylpiperazin-1-yl)-ethyl ether

A mixture of 14,4 g (0.05 mol) α-methylbenzoin 2-chlorethyl ether and 90 g (0.9 mol) N-methylpiperazine is stirred for 3 hours at 20° C. A small amount of formed precipitate is filtered off and the filtrate is stirred for 3.5 hours at 110° C. After cooling the reaction mixture is dissolved in ether and extracted first with cold water and afterwards with diluted hydrochloric acid. The acid solution is made strongly alkaline by neutralisation with caustic soda.

The alkaline solution is extracted with ether. The ethereal solution is dried over $Na_2SO_4$ and evaporated. The oily residue is dissolved in ether and this solution is purified by treating with carbon black and aluminium oxide, filtered and evaporated again. The residue begins to cristallise on standing and is rericstallised from hexane.

Mp. 75° C. Analysis: 8.0% N (theor. 7.95%)

EXAMPLE 12

α-Methylbenzoin 2-morpholinoethyl ether

A mixture of 17.5 g (0.06 mol) α-methylbenzoin 2-chloroethyl ether and 87 g (1 mol) morpholine are stirred 2 hours at 100° C. and 3 hours at 120° C. The reaction mixture is dissolved in ether and extracted first with ice water and then with diluted hydrochloric acid. The acid solution is made alkaline by neutralisation with $K_2CO_3$ and the alkaline solution is extracted with ether repeatedly. The ethereal solution is dried over $Na_2SO_4$ and evaporated. The oily residue is dissolved in methylene chloride and purified over a silicagel column. The product obtained by evaporation is a colourless oil.

Analysis: C: 73.5%; H: 7.2%; N: 4.0%; calculated C: 74.3%; H: 7.4%; N: 4.1%.

What is claimed is:

1. A compound of formula I

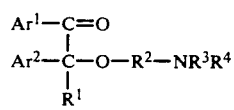

wherein $Ar^1$ and $Ar^2$, each independently of the other, represent phenyl or phenyl which is substituted by $C_1$-$C_4$-alkyl, $C_1$-$C_4$-alkoxy or halogen, $R^1$ represents a group $-O-R^2-N(R^3)(R^4)$, $R^2$ represents $C_2$-$C_4$-alkylene, $R^3$ represents hydrogen, $C_1$-$C_{12}$-alkyl, allyl, benzyl, cyclohexyl, $C_2$-$C_4$-hydroxyalkyl or $C_3$-$C_8$-alkoxyalkyl, and $R^4$ represents $C_1$-$C_{12}$-alkyl, allyl, $C_2$-$C_4$-hydroxyalkyl, $C_3$-$C_8$-alkoxyalkyl, cyclohexyl, benzyl or phenyl, or $R^3$ and $R^4$ together represent alkylene of 4 to 5 carbon atoms, 3-oxapentamethylene, or a group $-CH_2-CH_2-NR_5-CH_2-CH_2-$ and $R^5$ represents hydrogen or $C_1$-$C_4$-alkyl.

2. A compound of the formula I according to claim 1, wherein $Ar^1$ and $Ar^2$ represent phenyl, $R^1$ represents a group $-O-R^2-NR^3R^4$, $R^2$ represents 1,2-ethylene and each of $R^3$ and $R^4$ represents $C_1$-$C_4$-alkyl or $R^3$ and $R^4$ together represent $-(CH_2)_5$, $-CH_2CH_2OCH_2CH_2-$ or $-CH_2CH_2-NR^5-CH_2CH_2-$, wherein $R^5$ represents hydrogen or $CH_3$.

3. The compound according to claim 1 which is 2,2,-di-(2-diethylaminoethoxy)-1,2-diphenyl-ethanone.

4. The compound according to claim 1 which is 2,2-di-(2-piperidinoethoxy)-1,2-diphenyl-ethanone.

5. The compound of the formula

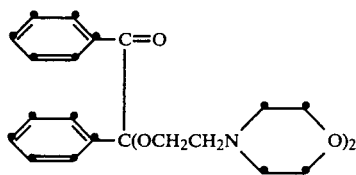

according to claim 1.

6. The compound of the formula

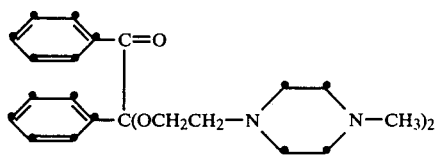

according to claim 1.

* * * * *

UNITED STATES PATENT AND TRADEMARK OFFICE
CERTIFICATE OF CORRECTION

PATENT NO. : 4,271,294
DATED : JUNE 2, 1981
INVENTOR(S) : LOUIS FELDER, RUDOLF KIRCHMAYR AND RINALDO HÜSLER

It is certified that error appears in the above—identified patent and that said Letters Patent is hereby corrected as shown below:

COVER PAGE, SECTION 75 INVENTORS, READ:

"[75] Inventors: Louis Felder, Basel; Rudolf Kirchmayr, Aesch; Rinaldo Küsler, Binningen, all of Switzerland".

Should read:

"[75] Inventors: Louis Felder, Basel; Rudolf Kirchmayr, Aesch; Rinaldo Hüsler, Binningen, all of Switzerland".

Signed and Sealed this

Third Day of November 1981

[SEAL]

Attest:

GERALD J. MOSSINGHOFF

Attesting Officer     Commissioner of Patents and Trademarks